United States Patent
Sakaguchi

(10) Patent No.: US 10,342,501 B2
(45) Date of Patent: Jul. 9, 2019

(54) X-RAY IMAGING APPARATUS, MEDICAL IMAGE PROCESSING APPARATUS, X-RAY IMAGING METHOD AND MEDICAL IMAGE PROCESSING METHOD

(71) Applicant: TOSHIBA MEDICAL SYSTEMS CORPORATION, Otawara (JP)

(72) Inventor: Takuya Sakaguchi, Utsunomiya (JP)

(73) Assignee: TOSHIBA MEDICAL SYSTEMS CORPORATION, Otawara-shi (JP)

( * ) Notice: Subject to any disclaimer, the term of this patent is extended or adjusted under 35 U.S.C. 154(b) by 117 days.

(21) Appl. No.: 14/205,970

(22) Filed: Mar. 12, 2014

(65) Prior Publication Data

US 2014/0192960 A1 Jul. 10, 2014

Related U.S. Application Data

(63) Continuation of application No. PCT/JP2013/060711, filed on Apr. 9, 2013.

(30) Foreign Application Priority Data

May 9, 2012 (JP) .................................. 2012-107936

(51) Int. Cl.
G03B 35/22 (2006.01)
G03B 42/02 (2006.01)
(Continued)

(52) U.S. Cl.
CPC ............ *A61B 6/5235* (2013.01); *A61B 6/022* (2013.01); *A61B 6/0457* (2013.01); *A61B 6/46* (2013.01);
(Continued)

(58) Field of Classification Search
CPC .. A61B 6/00; A61B 6/02; A61B 6/027; A61B 6/04; A61B 6/0457; A61B 6/46;
(Continued)

(56) References Cited

U.S. PATENT DOCUMENTS 5,034,987 A * 7/1991 Fujimoto ............... A61B 6/463
382/131
5,090,038 A * 2/1992 Asahina ................ A61B 6/022
348/E13.001

(Continued)

FOREIGN PATENT DOCUMENTS

CN 101228798 A 7/2008
JP 4-166135 A 6/1992
(Continued)

OTHER PUBLICATIONS

International Preliminary Report on Patentability and Written Opinion issued Nov. 20, 2014 in PCT/JP2013/060711 (submitting English language translation only).
(Continued)

*Primary Examiner* — Anastasia Midkiff
(74) *Attorney, Agent, or Firm* — Oblon, McClelland, Maier & Neustadt, L.L.P.

(57) ABSTRACT

According to one embodiment, an X-ray imaging apparatus includes an X-ray image acquisition unit, a control system and a display processing part. The X-ray image acquisition unit acquires X-ray image data of an object by using at least one imaging system. The control system controls the imaging system to acquire X-ray image data corresponding to different directions by reciprocating the imaging system repeatedly. The display processing part acquires X-ray image data for stereoscopic viewing out of the X-ray image data corresponding to the different directions to generate and display stereoscopically visible image data on a display unit based on the X-ray image data for the stereoscopic viewing. The X-ray image data for the stereoscopic viewing are acquired in a period without a motion or a possibility of the motion in an imaging part of the object.

11 Claims, 9 Drawing Sheets

(51) Int. Cl.
    *H04N 13/00*     (2018.01)
    *A61B 6/00*     (2006.01)
    *A61B 6/04*     (2006.01)
    *A61B 6/02*     (2006.01)

(52) U.S. Cl.
    CPC .............. *A61B 6/461* (2013.01); *A61B 6/463* (2013.01); *A61B 6/464* (2013.01); *A61B 6/466* (2013.01); *A61B 6/5264* (2013.01); *G03B 42/026* (2013.01); *A61B 6/486* (2013.01); *A61B 6/5205* (2013.01); *A61B 6/54* (2013.01); *G01N 2223/414* (2013.01); *G03B 35/22* (2013.01); *H04N 2013/0085* (2013.01)

(58) Field of Classification Search
    CPC ......... A61B 6/461; A61B 6/462; A61B 6/463; A61B 6/464; A61B 6/466; H01J 37/147; H01J 37/1478; G01N 2223/40; G01N 2223/414; G03B 42/00; G03B 42/02; G03B 42/026; G03B 35/00; G03B 35/02; G03B 35/18; G03B 35/20; G03B 35/22; H04N 13/0055; H04N 13/02; H04N 13/0203; H04N 13/0282; H04N 2013/0085; G06T 15/00
    See application file for complete search history.

(56) References Cited

U.S. PATENT DOCUMENTS

| | | | | |
|---|---|---|---|---|
| 5,448,610 | A * | 9/1995 | Yamamoto | A61B 6/022<br>348/E13.005 |
| 5,598,453 | A * | 1/1997 | Baba | A61B 6/032<br>378/146 |
| 6,233,003 | B1 * | 5/2001 | Ono | H04N 13/021<br>348/47 |
| 2007/0248319 | A1 * | 10/2007 | Sakaguchi | A61B 6/461<br>386/219 |
| 2008/0198219 | A1 | 8/2008 | Yoshida et al. | |
| 2009/0238334 | A1 * | 9/2009 | Brahme | A61B 6/022<br>378/41 |
| 2009/0257551 | A1 * | 10/2009 | Dafni | A61B 6/022<br>378/6 |
| 2009/0262891 | A1 * | 10/2009 | Zhang | G01B 15/00<br>378/57 |
| 2011/0216166 | A1 * | 9/2011 | Takahashi | H04N 13/02<br>348/46 |
| 2013/0155204 | A1 * | 6/2013 | Kokubun | G03B 35/02<br>348/49 |
| 2014/0198897 | A1 * | 7/2014 | Sakaguchi | A61B 6/022<br>378/37 |
| 2014/0205061 | A1 * | 7/2014 | Sakaguchi | A61B 6/486<br>378/41 |

FOREIGN PATENT DOCUMENTS

| | | |
|---|---|---|
| JP | 07-240944 A | 9/1995 |
| JP | 2006-136741 A | 6/2006 |
| JP | 2007-28295 A | 2/2007 |
| JP | 2009-017322 A | 1/2009 |
| JP | 2011-200408 | 10/2011 |

OTHER PUBLICATIONS

International Search Report dated Jul. 16, 2013 for PCT/JP2013/060711 filed on Apr. 9, 2013 with Translation of Categories.
International Written Opinion dated Jul. 16, 2013 for PCT/JP2013/060711 filed on Apr. 9, 2013.
Combined Office Action and Search Report dated Feb. 3, 2015 in Chinese Patent Application No. 201380000796.4 (with English translation of category of cited Documents).
Office Action dated Mar. 8, 2016 in Japanese Patent Application No. 2012-107936.

* cited by examiner

X-RAY IMAGING APPARATUS, MEDICAL IMAGE PROCESSING APPARATUS, X-RAY IMAGING METHOD AND MEDICAL IMAGE PROCESSING METHOD

CROSS REFERENCES TO RELATED APPLICATIONS

This is a continuation of Application PCT/JP2013/60711, filed Apr. 9, 2013.

This application is based upon and claims the benefit of priority from Japanese Patent Application No. 2012-107936, filed May 9, 2012; the entire contents of which are incorporated herein by reference.

FIELD

Embodiments described herein relate generally to an X-ray imaging apparatus, a medical image processing apparatus, an X-ray imaging method and a medical image processing method.

BACKGROUND

Conventionally, a technology for displaying X-ray diagnostic images which allow stereoscopically viewing an imaging target, such as a blood vessel, using an X-ray imaging apparatus has been proposed. Assuming that images which allow stereoscopic viewing of an imaging target are referred to as 3D (three dimensional) images, it is necessary to make an image for left eye and an image for right eye visible individually by the left eye and the right eye respectively in order to display one frame of 3D image.

Examples of method of respectively acquiring images for left eye and right eye using an X-ray imaging apparatus include a method of respectively acquiring 2D (two dimensional) X-ray projection images for left eye and right eye actually besides a method by image reconstruction processing. The X-ray projection images for left eye and right eye can be also acquired by an X-ray imaging apparatus having a single X-ray imaging system as well as an X-ray imaging apparatus having plural X-ray imaging systems.

In case of using an X-ray imaging apparatus having a single X-ray imaging system, the X-ray imaging system is positioned to the first position by moving the C-shaped arm of the X-ray imaging apparatus. Then, an X-ray projection image for left eye corresponding to the first position can be acquired with stopping the X-ray imaging system. Next, the C-shaped arm of the X-ray imaging apparatus are moved to position the X-ray imaging system to the second position. Then, an X-ray projection image for right eye corresponding to the second position can be acquired with stopping the X-ray imaging system. Alternatively, the X-ray projection images for left eye may be acquired after acquiring the X-ray projection images for right eye.

On the other hand, X-ray projection images for left eye and right eye can be acquired using an X-ray imaging apparatus having two X-ray imaging systems. In this case, the X-ray projection images for left eye and right eye can be acquired at a same timing by positioning the two X-ray imaging systems appropriately.

The X-ray projection images for left eye and right eye acquired as described above can be used as two-parallax images for displaying a 3D image. As a method of displaying one set of two-parallax images as a 3D image allowing stereoscopic viewing, a method of displaying images for left eye and right eye alternately with a time division so as to be viewed through a dedicated glasses, a method of displaying images for left eye and right eye on a dedicated display without using a glasses, and the like are known.

Especially, acquiring X-ray projection images for left eye and right eye at a same timing using an X-ray imaging apparatus having two X-ray imaging systems makes it possible to display a 3D image, having an improved image quality, less influenced by a motion of an object.

Furthermore, generating two-parallax images by image reconstruction processing makes it possible to display 3D images allowing stereoscopic viewing from various observation directions.

PRIOR TECHNICAL LITERATURE

[Patent literature 1] JPA H04-166135

However, there is a problem that the X-ray imaging apparatus having plural X-ray imaging systems has a complex structure and is expensive. Moreover, when a 3D image for stereoscopic viewing is generated by image reconstruction processing, there is a problem that a data processing amount becomes huge and a data processing time also becomes long.

Accordingly, an object of the present invention is to provide an X-ray imaging apparatus, a medical image processing apparatus, an X-ray imaging method and a medical image processing method by which X-ray images useful for a diagnosis can be displayed as a 3D image for stereoscopic viewing with a simpler and more inexpensive structure.

DETAILED DESCRIPTION

Figure 1:
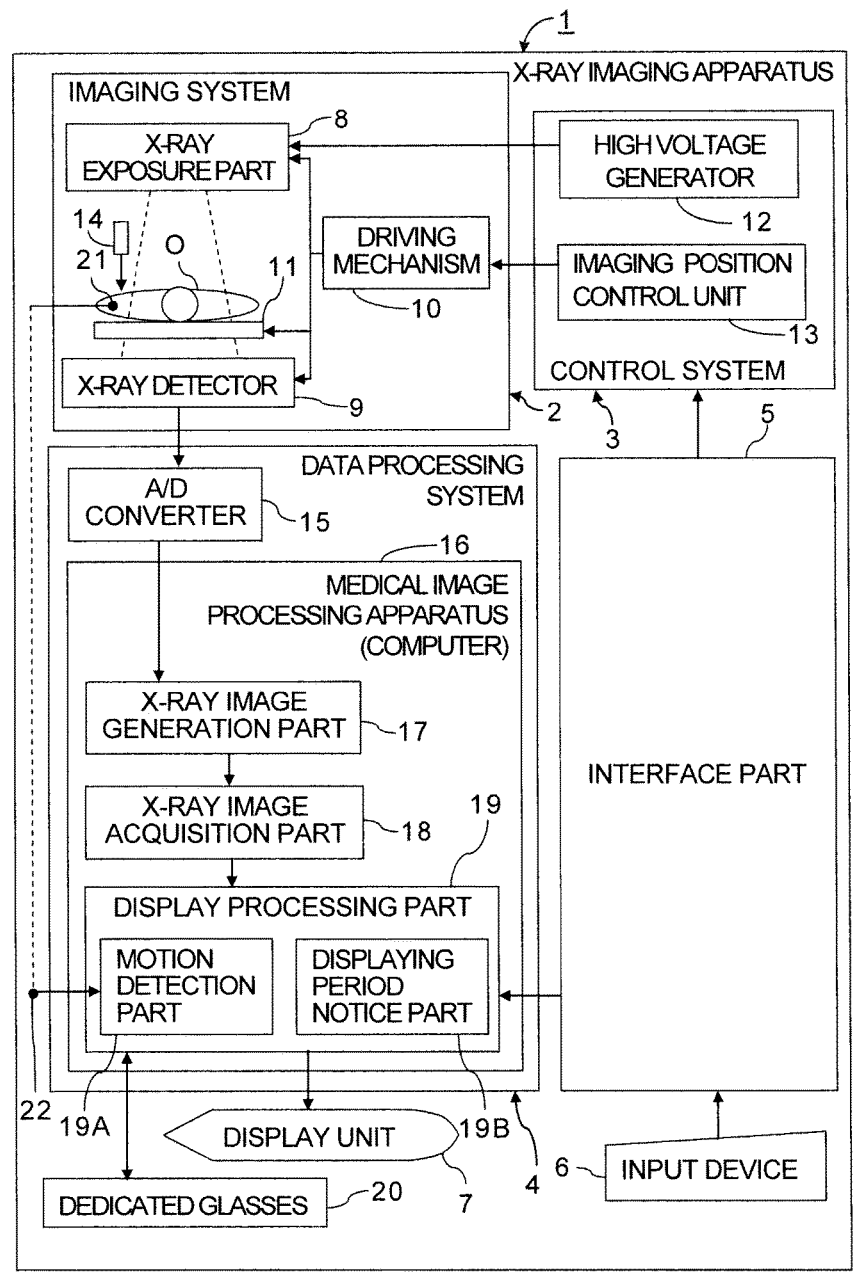
FIG. 1 is a configuration diagram of an X-ray imaging apparatus and a medical image processing apparatus according to one embodiment of the present invention.

In general, according to one embodiment, an X-ray imaging apparatus includes an X-ray image acquisition unit, a control system and a display processing part. The X-ray image acquisition unit is configured to acquire X-ray image data of an object by using at least one imaging system. The control system is configured to control the imaging system to acquire frames of X-ray image data corresponding to mutually different directions by reciprocating the imaging system repeatedly. The display processing part is configured to acquire frames of X-ray image data for stereoscopic viewing out of the frames of the X-ray image data corresponding to the different directions to generate and display stereoscopically visible image data on a display unit based on the acquired frames of the X-ray image data for the stereoscopic viewing. The frames of the X-ray image data for the stereoscopic viewing are acquired in a period without a motion or a possibility of the motion in an imaging part of the object.

Further, according to another embodiment, an X-ray imaging apparatus includes an X-ray image acquisition unit, a control system and a display processing part. The X-ray image acquisition unit is configured to acquire X-ray image data of an object by using at least one imaging system. The control system is configured to control the imaging system to acquire frames of X-ray image data corresponding to mutually different directions by reciprocating the imaging system repeatedly. The display processing part is configured to output a notice to an output device to generate and display stereoscopically visible image data on a display unit based on frames of X-ray image data acquired a period according to an output timing of the notice. The notice is for permitting or prohibiting a possible motion in an imaging part of the object.

Further, according to another embodiment, a medical image processing apparatus includes an image acquisition part and a display processing part. The image acquisition part is configured to acquire frames of X-ray image data of an object corresponding to mutually different directions. The frames of the X-ray image data are acquired by reciprocating a single imaging system repeatedly. The display processing part is configured to acquire frames of X-ray image data for stereoscopic viewing out of the frames of the X-ray image data acquired by said X-ray image acquisition unit to generate and display stereoscopically visible image data on a display unit based on the acquired frames of the X-ray image data for the stereoscopic viewing. The frames of the X-ray image data for the stereoscopic viewing are acquired in a period without a motion or a possibility of the motion in an imaging part of the object.

Further, according to another embodiment, a medical image processing apparatus includes an image acquisition part and a display processing part. The image acquisition part is configured to acquire frames of X-ray image data of an object corresponding to mutually different directions. The frames of the X-ray image data are acquired by reciprocating a single imaging system repeatedly. The display processing part is configured to output a notice to an output device to generate and display stereoscopically visible image data on a display unit based on frames of X-ray image data acquired a period according to an output timing of the notice. The notice is for permitting or prohibiting a possible motion in an imaging part of the object.

Further, according to another embodiment, an X-ray imaging method includes: acquiring X-ray image data of an object by using at least one imaging system; controlling the imaging system to acquire frames of X-ray image data corresponding to mutually different directions by reciprocating the imaging system repeatedly; and acquiring frames of X-ray image data for stereoscopic viewing out of the frames of the X-ray image data corresponding to the different directions to generate and display stereoscopically visible image data on a display unit based on the acquired frames of the X-ray image data for the stereoscopic viewing. The frames of the X-ray image data for the stereoscopic viewing are acquired in a period without a motion or a possibility of the motion in an imaging part of the object.

Further, according to another embodiment, an X-ray imaging method includes: acquiring X-ray image data of an object by using at least one imaging system; controlling the imaging system to acquire frames of X-ray image data corresponding to mutually different directions by reciprocating the imaging system repeatedly; and outputting a notice to an output device to generate and display stereoscopically visible image data on a display unit based on frames of X-ray image data acquired a period according to an output timing of the notice. The notice is for permitting or prohibiting a possible motion in an imaging part of the object.

Further, according to another embodiment, a medical image processing method includes: acquiring frames of X-ray image data of an object corresponding to mutually different directions; and acquiring frames of X-ray image data for stereoscopic viewing out of the frames of the X-ray image data corresponding to the different directions to generate and display stereoscopically visible image data on a display unit based on the acquired frames of the X-ray image data for the stereoscopic viewing. The frames of the X-ray image data corresponding to the different directions are acquired by reciprocating a single imaging system repeatedly. The frames of the X-ray image data for the stereoscopic viewing are acquired in a period without a motion or a possibility of the motion in an imaging part of the object.

Further, according to another embodiment, a medical image processing method includes: acquiring frames of X-ray image data of an object corresponding to mutually different directions; and outputting a notice to an output device to generate and display stereoscopically visible image data on a display unit based on frames of X-ray image data acquired a period according to an output timing of the notice. The frames of the X-ray image data are acquired by reciprocating a single imaging system repeatedly. The notice is for permitting or prohibiting a possible motion in an imaging part of the object.

An X-ray imaging apparatus, a medical image processing apparatus, an X-ray imaging method and a medical image processing method according to embodiments of the present invention will be described with reference to the accompanying drawings.

FIG. 1 is a configuration diagram of an X-ray imaging apparatus and a medical image processing apparatus according to one embodiment of the present invention.

An X-ray imaging apparatus 1 includes an imaging system 2, a control system 3, and a data processing system 4, an interface part 5, an input device 6 and a display unit 7. The imaging system 2 has an X-ray exposure part 8, an X-ray detector 9, a driving mechanism 10 and a bed 11. The control system 3 has a high voltage generator 12 and an imaging position control unit 13.

The X-ray exposure part 8 includes an X-ray tube and is placed in the opposite side of the X-ray detector 9 so that an object O set on the bed 11 lies between the X-ray exposure part 8 and the X-ray detector 9. The X-ray exposure part 8 and the X-ray detector 9 can change the angle and the relative position with respect to the object O with keeping their relative position by driving the driving mechanism 10.

Specifically, the X-ray exposure part 8 and the X-ray detector 9 are settled at both ends of the C-shaped arm having the rotational function. Then, the X-ray exposure part 8 is configured to expose an X-ray from a predetermined angle to an object O by the X-ray tube to detect the X-ray having transmitted the object O by the X-ray detector 9.

Moreover, the incline and the position of the table of the bed 11 can be adjusted with the driving mechanism 10. Therefore, the radiation direction of an X-ray toward an object O can be changed by adjusting not only the angle of the X-ray exposure part 8 and the X-ray detector 9 with regard to the object O but also the angle of the table.

Furthermore, a contrast medium injector 14 is provided in the vicinity of the object O set on the bed 11 in order to inject a contrast agent into the object O, as needed.

The high voltage generator 12 of the control system 3 is a unit which applies a high voltage to the X-ray tube of the X-ray exposure part 8 to expose an X-ray, having a desired energy, toward the object O. The imaging position control unit 13 is a unit which outputs a control signal to the driving mechanism 10 to control the driving mechanism 10. That is, the inclination and position of the top plate of the bed 11, and the rotation angle and position of the X-ray exposure part 8 and the X-ray detector 9 are controlled by the control signal output to the driving mechanism 10 from the imaging position control unit 13.

The data processing system 4 has an A/D (analog to digital) converter 15 and a computer 16. The computer 16 functions as a medical image processing apparatus 16 by executing programs. That is, the medical image processing apparatus 16 is built in the X-ray imaging apparatus 1.

However, an independent medical image processing apparatus having the similar function may be connected to the X-ray imaging apparatus 1 through a network. Moreover, circuits may be used for configuring the medical image processing apparatus 16 built in the X-ray imaging apparatus 1 or the medical image processing apparatus connected with the X-ray imaging apparatus 1 through a network. Meanwhile, the computer 16 may function as the interface part 5.

The medical image processing apparatus 16 has an X-ray image generation part 17, an X-ray image acquisition part 18 and a display processing part 19. The X-ray image generation part 17 has a function to read digitized X-ray detection data from the X-ray detector 9 through the A/D converter 15 to generate X-ray image data by data processing of the read X-ray detection data.

Therefore, the X-ray imaging apparatus 1 has a function as an X-ray image acquisition unit, which acquires X-ray image data of an object O using the imaging system 2, by collaboration of the X-ray image generation part 17 with the imaging system 2 and the control system 3.

The X-ray image acquisition part 18 has a function to acquire the X-ray image data generated in the X-ray image generation part 17 and give the X-ray image data to the display processing part 19. Especially, in an independent medical image processing apparatus connected to the X-ray imaging apparatus 1 through a network, the X-ray image generation part 17 can be omitted. In this case, a function to acquire the X-ray image data from the X-ray image generation part 17 included in the X-ray imaging apparatus 1 through a network is provided with the X-ray image acquisition part 18.

The display processing part 19 has a function to acquire frames of X-ray image data including a frame of X-ray image data for left eye and a frame of X-ray image data for right eye from the X-ray image acquisition part 18; a function to generate 3D image data, as image data allowing stereoscopic viewing, based on the acquired frames of the X-ray image data; and a function to display the generated 3D image data on the display unit 7.

As a method of displaying a 3D image for stereoscopic viewing based on frames of X-ray image data for left eye and right eye, an arbitrary known method can be used. As typical methods, a method by using an usual display and a dedicated glasses and a method by using a dedicated display are known.

In case of using a dedicated glasses, a method of alternately indicating images for left eye and images for right eye with a constant temporal difference and preparing a function as a polarization plate with the dedicated glasses is known. In this case, circular polarized lights in mutually different rotational directions are given to the images for left eye and right eye. Thus, using a circular light glasses makes two-parallax images visible individually by the left and right eyes.

Alternatively, a method of indicating an image for left eye and an image for right eye as images in mutually different bands of wavelength with a time division is also known. In this case, the image for left eye and the image for right eye, which have transmitted a filter to become lights in the mutually different bands of wavelength, are visually recognized by the left and right eyes individually through a wavelength selection glasses.

Furthermore, another method for indicating images for left eye and images for right eye alternately with a time division so that the images for left eye and the images for right eye can be visually recognized with a glasses whose shutters for left eye and right eye open and close in synchronized with the time division is also known.

Conversely, a method for outputting positional information and directional information from a dedicated glasses and changing images to be output on a display according to the positional information and the directional information of the glasses is also known.

On the other hand, as a method without using a dedicated glasses, a method of overlapping a wave plate, having a phase difference, on the surface of a display, a method of overlapping a film, on which a convexoconcave having lines per inch different from a resolution of a display is arranged, on the surface of the display, and the like are known. Each of these methods is also called a spatial division method by which images for left eye and images for right eye are visually recognized by the left and right eyes respectively through a wave plate or a film.

Therefore, the X-ray imaging apparatus 1 has elements according to a displaying method of a 3D image. For example, a dedicated glasses 20 is connected with the computer 16 when it is required for the 3D display. Moreover, a dedicated display for 3D display is connected as the display unit 7 with the computer 16 when it is required for the 3D display. Thus, the display processing part 19 is configured to output and input information required for 3D display to one or both of the display unit 7 and the glasses 20.

On the other hand, the control system 3 has a function to control the single imaging system 2 in order to acquire frames of X-ray image data for left eye and right eye required for stereoscopic viewing. Specifically, the control system 3 has a function to control the imaging system 2 so that frames of X-ray image data corresponding to mutually different directions are acquired by reciprocating the single imaging system 2 repeatedly. Such control allows the X-ray image acquisition part 18 to obtain frames of X-ray image data of an object O corresponding to mutually different directions.

Then, the display processing part 19 is configured to generate X-ray image data for 3D display by display processing according to acquisition positions of frames of X-ray image data acquired with reciprocating the single imaging system 2. Specifically, one frame of image data which can be stereoscopically viewed can be generated using two frames of X-ray image data, corresponding to mutually different two directions, as two-parallax image data.

Figure 2:
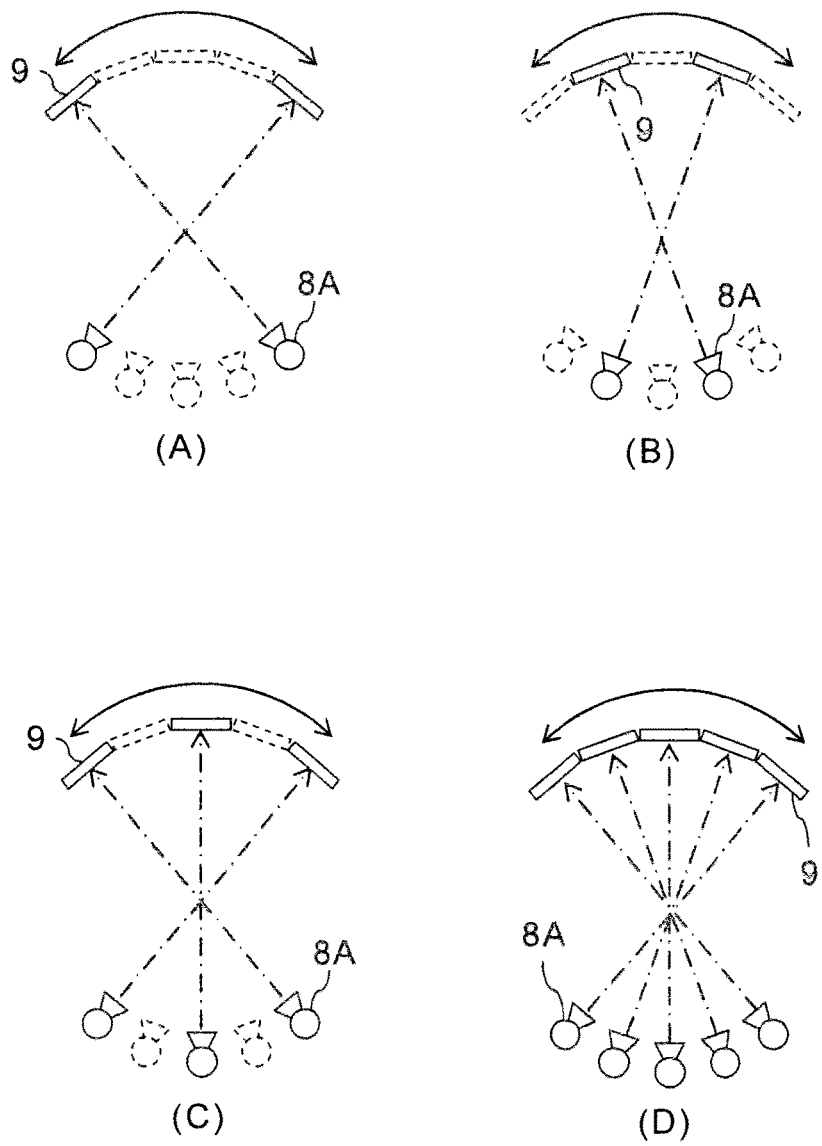
FIG. 2 shows examples of control method of the imaging system, for displaying X-ray images which can be stereoscopically viewed, in the X-ray imaging apparatus shown in FIG. 1.

FIG. 2 shows examples of control method of the imaging system 2, for displaying X-ray images which can be stereoscopically viewed, in the X-ray imaging apparatus 1 shown in FIG. 1.

As shown in FIG. 2 (A), imaging can be repeated by continuously moving the C-shaped arm to move the imaging system 2 like a pendulum. Specifically, the X-ray tube 8A of the X-ray exposure part 8 and the X-ray detector 9 can be reciprocated by driving the driving mechanism 10, and two frames of X-ray image data corresponding to the both end points of the X-ray tube 8A and the X-ray detector 9 can be sequentially acquired. Then, the two frames of X-ray image data corresponding to the two different X-ray exposure directions can be used as X-ray image data, having a two-parallax, for one frame.

Figure 3:
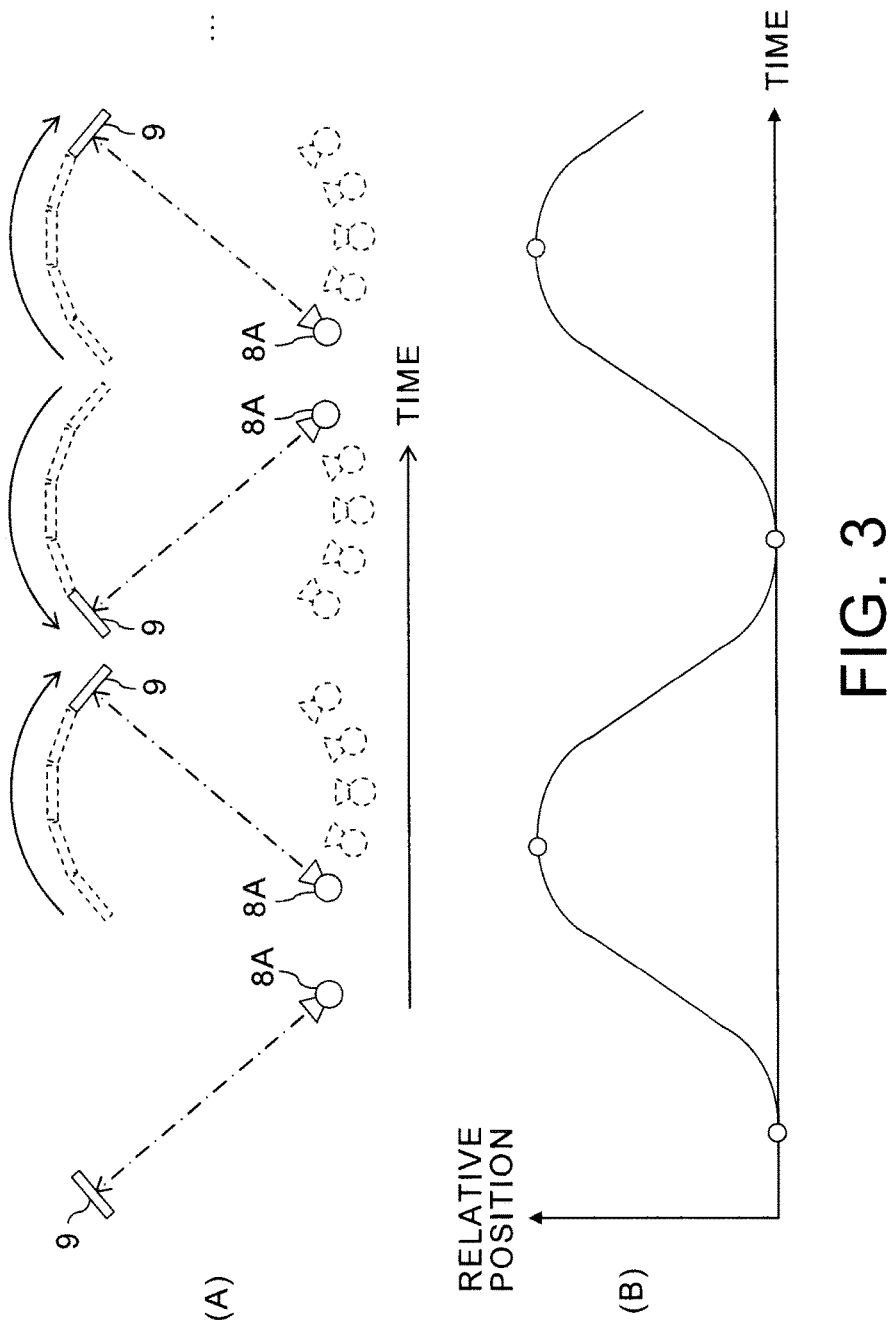
FIG. 3 shows the acquisition positions of X-ray image data in a time series in case of moving the X-ray tube and the X-ray detector as shown in FIG. 2 (A)

FIG. 3 shows the acquisition positions of X-ray image data in a time series in case of moving the X-ray tube 8A and the X-ray detector 9 as shown in FIG. 2 (A).

In FIG. 3 (A), the horizontal axis direction represents time. FIG. 3 (A) shows positions of the X-ray tube 8A and the X-ray detector 9 at acquisition timings of frames of X-ray image data. Moreover, FIG. 3 (B) is a graph each showing a time change in the relative position of the imaging system 2 including the X-ray tube 8A and the X-ray detector 9. That is, in FIG. 3 (B) 4, the horizontal axis represents time while the vertical axis represents the relative position of the imaging system 2.

When the X-ray tube 8A and the X-ray detector 9 are reciprocated as shown in FIG. 2 (A), X-ray image data for left eye and X-ray image data for right eye are sequentially and alternately acquired as shown in FIG. 3 (A). Therefore, the X-ray image data for left eye and the X-ray image data for right eye are alternately updated and indicated by the display processing part 19.

Note that, the velocity of the X-ray tube 8A and the X-ray detector 9 temporarily becomes zero at the turning points of the X-ray tube 8A and the X-ray detector 9. Therefore, as shown in FIG. 3 (B), the X-ray tube 8A and the X-ray detector 9 don't maintain a constant velocity, and the position of the X-ray tube 8A and the X-ray detector 9 changes periodically and nonlinearly like a pendulum motion. Then, as the marking points of FIG. 3 (B) show, the acquisition positions of the X-ray image data are at the local maximum and the local minimum.

The X-ray image data for left eye will be an image data corresponding to the same exposure direction of X-ray constantly. Similarly, the X-ray image data for right eye will be an image data corresponding to the same exposure direction of X-ray constantly. Therefore, when the X-ray image data for left eye and the X-ray image data for right eye are sequentially updated and displayed as a 3D image, the 3D image will be like a moving image in one observation direction.

However, a gantry having a C-shaped arm has a relatively large weight and a large force of inertia. For this reason, to acquire one frame of X-ray image data after acquiring another one frame of X-ray image data by moving a C-shaped arm, accelerations and stops of the heavy C-shaped arm are required. Therefore, an acquisition interval between two frames of X-ray image data becomes relatively long. As the result, influence of a motion of the object O may not be ignored between an acquisition timing of X-ray image data for left eye and an acquisition timing of X-ray image data for right eye.

Then, the imaging system 2 can be controlled so as to acquire frames of X-ray image data during a movement of the imaging system 2 including the X-ray tube 8A and the X-ray detector 9. Specifically, as shown in FIG. 2 (B), the imaging system 2 can be controlled so as to acquire frames of X-ray image data corresponding to mutually different directions in each of the outward way and the return way with reciprocating the X-ray tube 8A and the X-ray detector 9. In this case, two frames of X-ray image data corresponding to different positions, which are not on the both ends of the movement range of the imaging system 2, are inevitably acquired.

Figure 4:
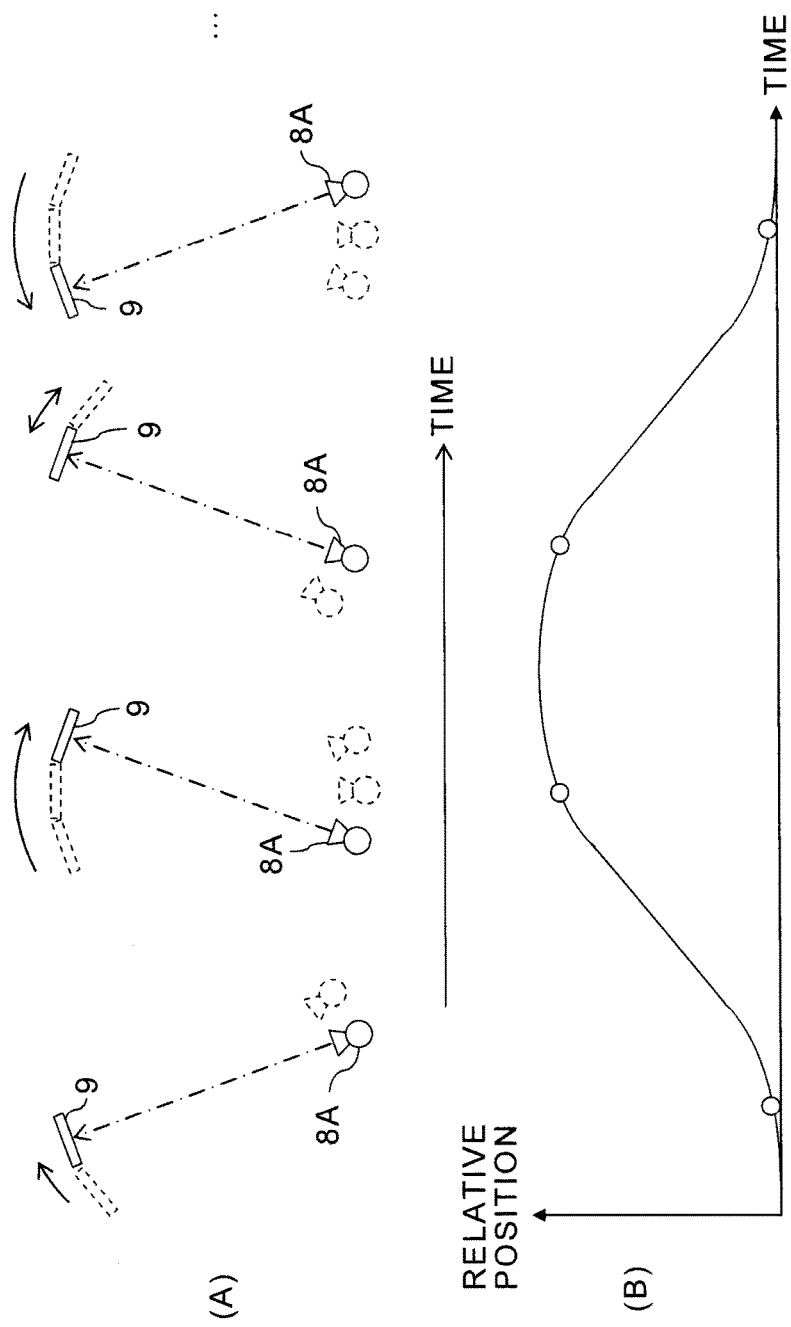
FIG. 4 shows the acquisition positions of X-ray image data in a time series in case of moving the X-ray tube and the X-ray detector as shown in FIG. 2 (B)

FIG. 4 shows the acquisition positions of X-ray image data in a time series in case of moving the X-ray tube 8A and the X-ray detector 9 as shown in FIG. 2 (B).

In FIG. 4 (A), the horizontal axis direction represents time. FIG. 4 (A) shows positions of the X-ray tube 8A and the X-ray detector 9 at acquisition timings of frames of X-ray image data. Moreover, FIG. 4 (B) is a graph each showing a time change in the relative position of the imaging system 2 including the X-ray tube 8A and the X-ray detector 9. That is, in FIG. 4 (B) 4, the horizontal axis represents time while the vertical axis represents the relative position of the imaging system 2.

When two frames of X-ray image data are acquired while the X-ray tube 8A and the X-ray detector 9 are reciprocated and they are moving as shown in FIG. 2 (B), X-ray image data for left eye and X-ray image data for right eye can be acquired at a short time interval as shown in FIG. 4 (A). Therefore, the scale of the time-axis shown in FIG. 4 (B) differs from the scale of the time-axis shown in FIG. 3 (B). Moreover, as the marking points of FIG. 4 (B) show, the acquisition positions of X-ray image data are two positions located between each local maximum and local minimum.

Moreover, not only the examples shown in FIG. 2 (B) and FIG. 4, the imaging system 2 can be controlled also as to acquire one frame of X-ray image data corresponding to mutually different directions in the outward way and the return way with reciprocating the imaging system 2.

Figure 5:
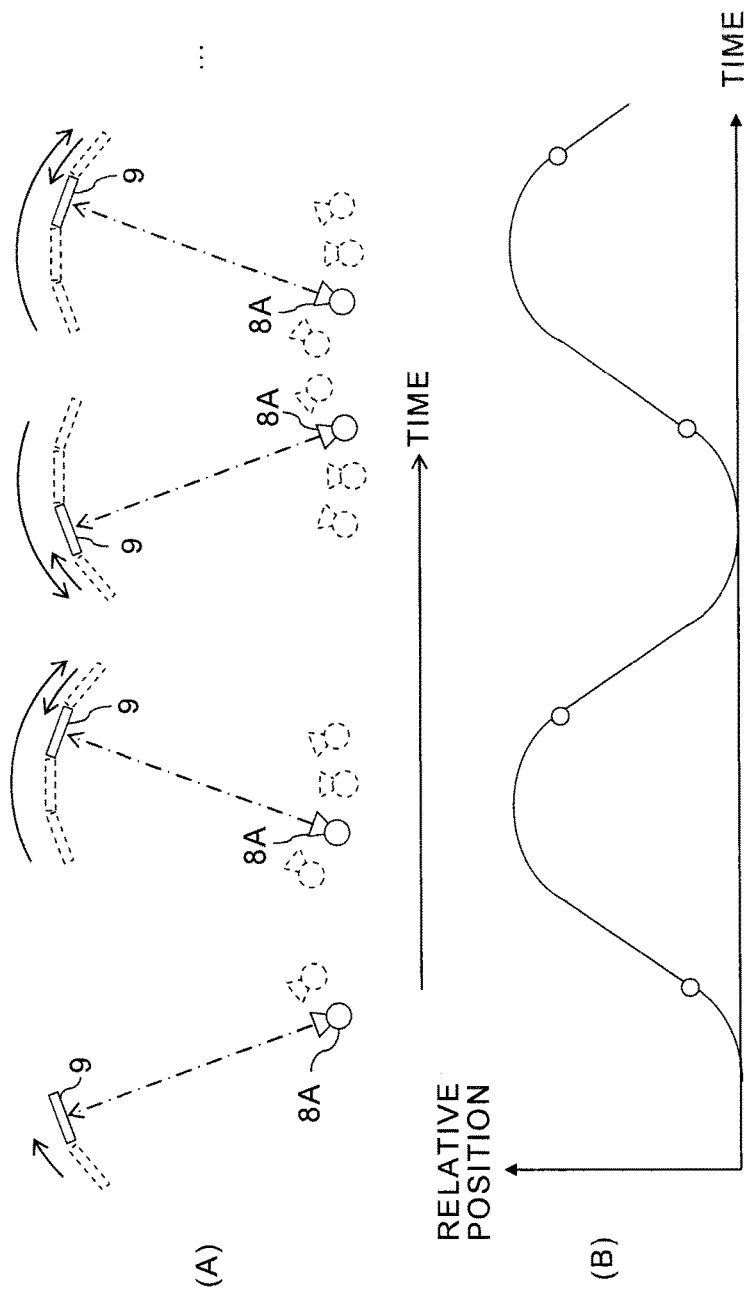
FIG. 5 shows the positions for acquiring frames of X-ray image data in a time series in case of acquiring X-ray image data for one frame in each of the accelerating periods in the outward way and the return way of the imaging system.

FIG. 5 shows the positions for acquiring frames of X-ray image data in a time series in case of acquiring X-ray image data for one frame in each of the accelerating periods in the outward way and the return way of the imaging system 2. Meanwhile, FIG. 6 shows the positions for acquiring frames of X-ray image data in a time series in case of acquiring X-ray image data for one frame in each of the decelerating periods in the outward way and the return way of the imaging system 2.

Figure 6:
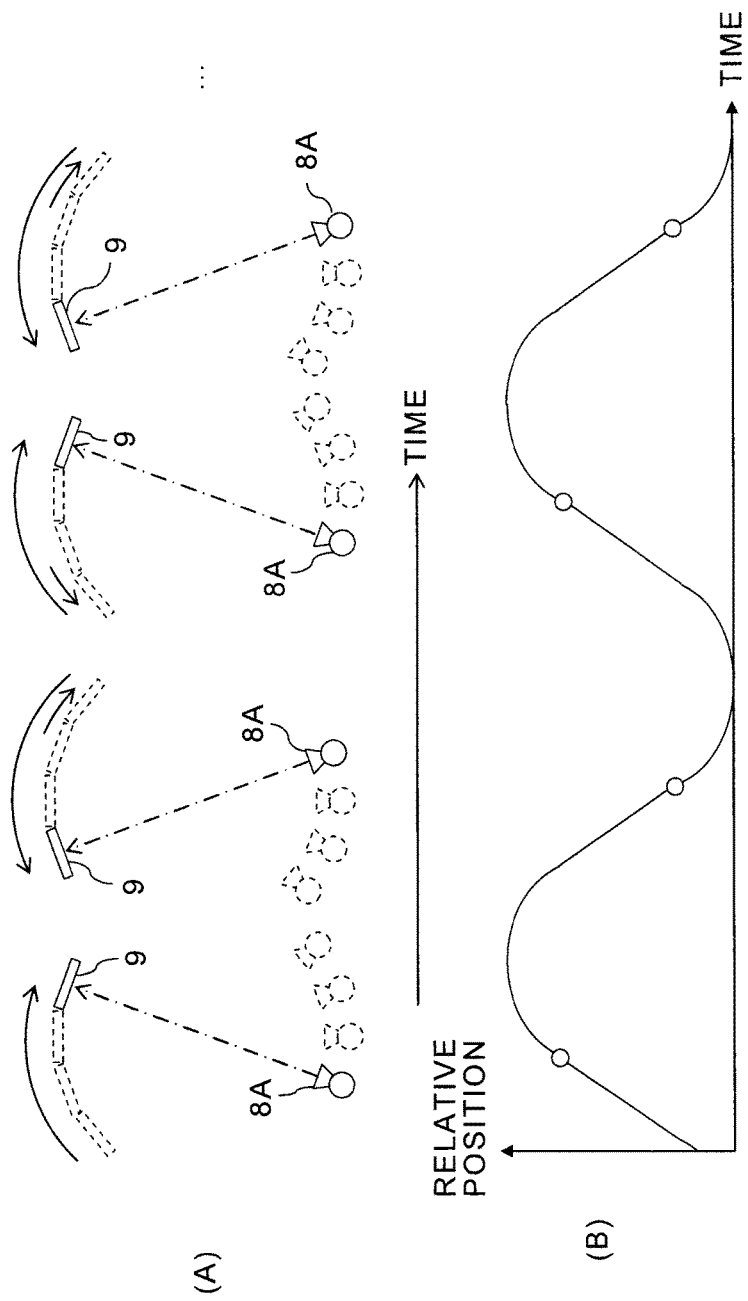
FIG. 6 shows the positions for acquiring frames of X-ray image data in a time series in case of acquiring X-ray image data for one frame in each of the decelerating periods in the outward way and the return way of the imaging system.

In FIG. 5 (A) and FIG. 6 (A), each horizontal axis direction represents time. FIG. 5 (A) and FIG. 6 (A) show positions of the X-ray tube 8A and the X-ray detector 9 at acquisition timings of frames of X-ray image data. Moreover, FIG. 5 (B) and FIG. 6 (B) are graphs each showing a time change in the relative position of the imaging system 2 including the X-ray tube 8A and the X-ray detector 9. That is, in each of FIG. 5 (B) and FIG. 6 (B), the horizontal axis represents time while the vertical axis represents the relative position of the imaging system 2.

As shown in FIG. 5, when X-ray image data is acquired while the X-ray tube 8A and the X-ray detector 9 move from one of the both ends of the movement range to the center position, X-ray image data to be acquired always in an accelerating period of the X-ray tube 8A and the X-ray detector 9. On the other hand, as shown in FIG. 6, when X-ray image data is acquired while the X-ray tube 8A and the X-ray detector 9 move from the center position of the movement range to one of the both ends, X-ray image data is to be acquired always in an decelerating period of the X-ray tube 8A and the X-ray detector 9.

Therefore, when the imaging system 2 is controlled as shown in FIG. 5 or FIG. 6, X-ray image data can be acquired under a mechanically equivalent condition. That is, frames of image data for left eye and frames of image data for right eye can be acquired when the imaging system 2 is at the same movement velocity in each acquisition time. For this reason, display of stable 3D images is attained.

Besides the above examples, X-ray image data other than X-ray image data for left eye and X-ray image data for right eye can be also acquired at an arbitrary position as shown in FIG. 2 (C). Then, the X-ray image data acquired at an arbitrary position can be used for display processing for a 3D display. In the example shown in FIG. 2 (C), the X-ray image data corresponding to the center position of the movement range of the imaging system 2 is acquired.

X-ray image data except for X-ray image data for left eye and X-ray image data for right eye can be used for arbitrary processing according to diagnostic purposes, such as compound processing with X-ray image data for left eye and X-ray image data for right eye.

FIG. 2 (A), (B), and (C) show some examples of control methods of the imaging system 2 for displaying X-ray images for which stereoscopic viewing is allowed from one direction. However, the imaging system 2 can be also controlled so as to display X-ray images for which stereoscopic viewing is allowed from plural directions. In order to display X-ray images for which stereoscopic viewing is allowed from plural directions, two or more different sets of two-parallax image data are required. Therefore, it is necessary to acquire some frames of X-ray image data corresponding to three or more different X-ray exposure directions.

Accordingly, the single imaging system 2 may be reciprocated like a pendulum as shown in FIG. 2 (D) so that frames of X-ray image data corresponding to mutually different three or more directions are acquired in each of the outward way and the return way. When the imaging system 2 is controlled by the control system 3 as shown in FIG. 2 (D), frames of X-ray image data, corresponding to mutually different three or more directions, acquired using the single imaging system 2 are acquired in the image acquisition part 18. For this reason, the display processing part 19 can generate 3D image data allowing stereoscopic viewing from plural directions, based on the frames of the X-ray image data corresponding to the different directions.

Figure 7:
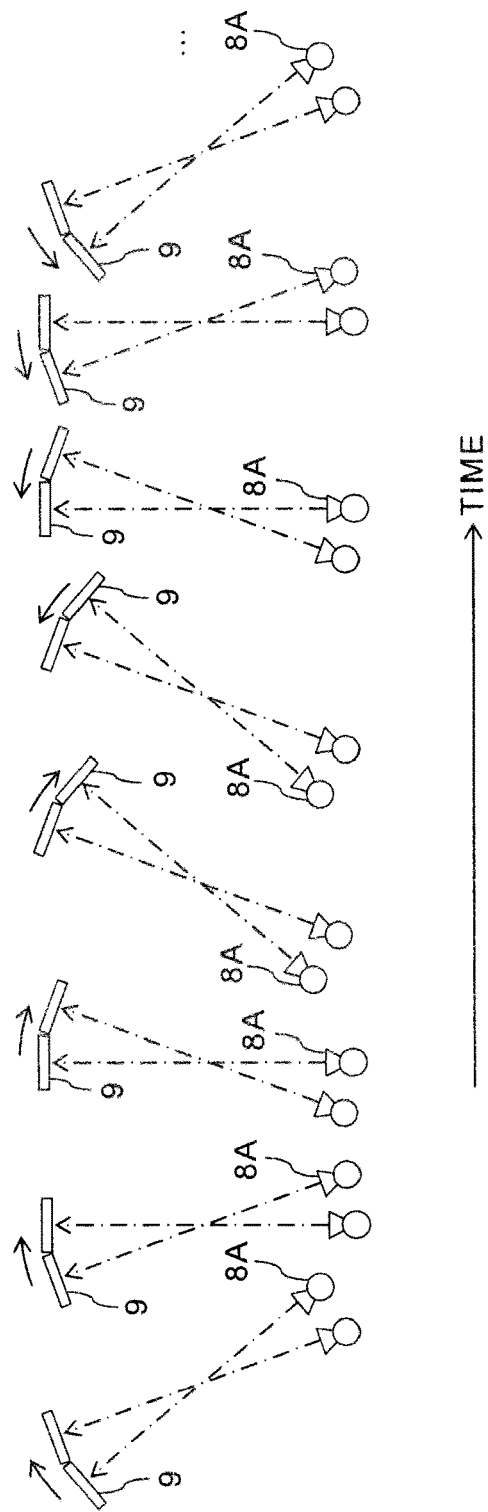
FIG. 7 is a view showing an example of display processing in the display processing part for displaying X-ray images which can be stereoscopically viewed from plural directions.

FIG. 7 is a view showing an example of display processing in the display processing part 19 for displaying X-ray images which can be stereoscopically viewed from plural directions.

In FIG. 7, the horizontal axis direction represents time. Moreover, the respective positions of the X-ray tube 8A and the X-ray detector 9 shown in FIG. 7 represent acquisition positions of frames of X-ray image data displayed as one frame of stereoscopic image.

As shown in FIG. 7, frames of image data, which can be stereoscopically viewed from mutually different directions, can be generated by sequentially generating one frame of image data, allowing stereoscopic viewing, based on two frames of X-ray image data corresponding to two different directions. That is, the imaging system 2 can be reciprocated continuously and a newly acquired image and an image acquired in the past can be indicated and updated as a pair of two-parallax images.

When the display control of stereoscopic images as shown in FIG. 7 is performed, one of images which constitute a stereoscopic image is updated and the pair of two-parallax images changes whenever a new image is acquired. Therefore, the stereoscopic images serve as a moving image to which the viewpoint changes sequentially. Accordingly, an imaged target is to be seen with a rotation.

Note that, images which are not adjacent may be used as a pair of two-parallax images although the adjacent images are used as a pair of two-parallax images in the examples shown in FIG. 7. It is experientially suitable for effective stereoscopic viewing that the difference in angle between exposure directions of X-rays exposed in order to acquire two images used as a pair of two-parallax images is set within the range from 1 degree to 3 degrees. Therefore, it is most effective to set the angle difference, between X-ray exposure directions corresponding to a pair of two-parallax images, to 2 degrees.

However, in order to achieve stereoscopic viewing, it is necessary to be able to ignore a motions of an imaging part of the object O in an acquisition period of image data for right eye and image data for left eye which constitute a pair of two-parallax image data. If an imaging part has a motion at an acquisition time for a pair of two-parallax image, a sense of discomfort will arise and stereoscopic viewing will become difficult.

On the other hand, depending on a diagnostic purpose, a motion of an imaging part may not be avoidable. For example, in endovascular treatments which attract attentions in recent years, a device, such as a catheter or a wire, is inserted into a blood vessel, and it becomes an operation object. That is, it is required to operate a device with referring to X-ray images in real time.

Then, the display processing part 19 is configured to acquire frames of X-ray image data for stereoscopic viewing, acquired in a period without a motion or a motion possibility of an imaging part of the object O, out of frames of X-ray image data acquired by reciprocating the imaging system 2 like the above-mentioned example, and also configured to generate stereoscopically visible image data based on the acquired frames of X-ray image data for stereoscopic viewing to display them on the display unit 7.

For that purpose, the display processing part 19 has a motion detection part 19A and a displaying period notice part 19B. The motion detection part 19A has a function to detect a motion of an imaging part of the object O. A motion of an imaging part is detectable based on frames of acquired X-ray image data.

As an example, existence of a motion is detectable by comparing two frames of image data, corresponding to a same direction, with each other. Moreover, even from two frames of image data corresponding to different directions, existence of a motion is detectable by generating two frames of image data corresponding to a same direction by coordinate conversion processing.

As the motion detection processing, known processing can be used. For example, when a signal value of subtraction image data in an arbitrary region between two frames of image data exceeds a threshold value, it can be considered that there was a motion. Instead of a signal value of subtraction image data, an index of amount of divergence, such as least squares errors, between frames of image data may be used. As another example, when a cross-correlation function of two frames of image data becomes smaller than a threshold value, it can also be considered that there was a motion.

Moreover, when a device, such as a wire, is depicted in an X-ray image, the device can be used as a marker, and it can be considered that there was a motion in the case that a motion distance of the marker exceeds a threshold value. Therefore, the motion detection can be performed by edge detection processing of the device, and also performed by threshold processing of a motion distance of the device outline extracted by the edge detection processing of the device.

On the other hand, a sensor 21 may be inserted in an imaging part to detect a motion and the motion can be detected based on information from the sensor 21. In that case, the motion detection part 19A is configured to be able to acquire output signals from the sensor 21.

As a practicable example, a position sensor having a receiver such as a GPS (Global Positioning System) receiver can be attached with a device such as a wire. Then, an output signal from the position sensor can be received as a wireless signal, and a motion distance of the position sensor can be detected. Alternatively, a transmitter may be attached as the sensor 21 and a motion distance of the transmitter can be detected based on radio waves received from the transmitter. In such a case, a wireless receiving antenna 22 is installed in the data processing system 4, and the motion detection part 19A is configured to acquire output data from the receiving antenna 22.

Then, the display processing part 19 can be configured to avoid generating or displaying stereoscopically visible image data corresponding to a period according to a timing of a motion detection when a motion in an imaging part is detected.

Figure 8:
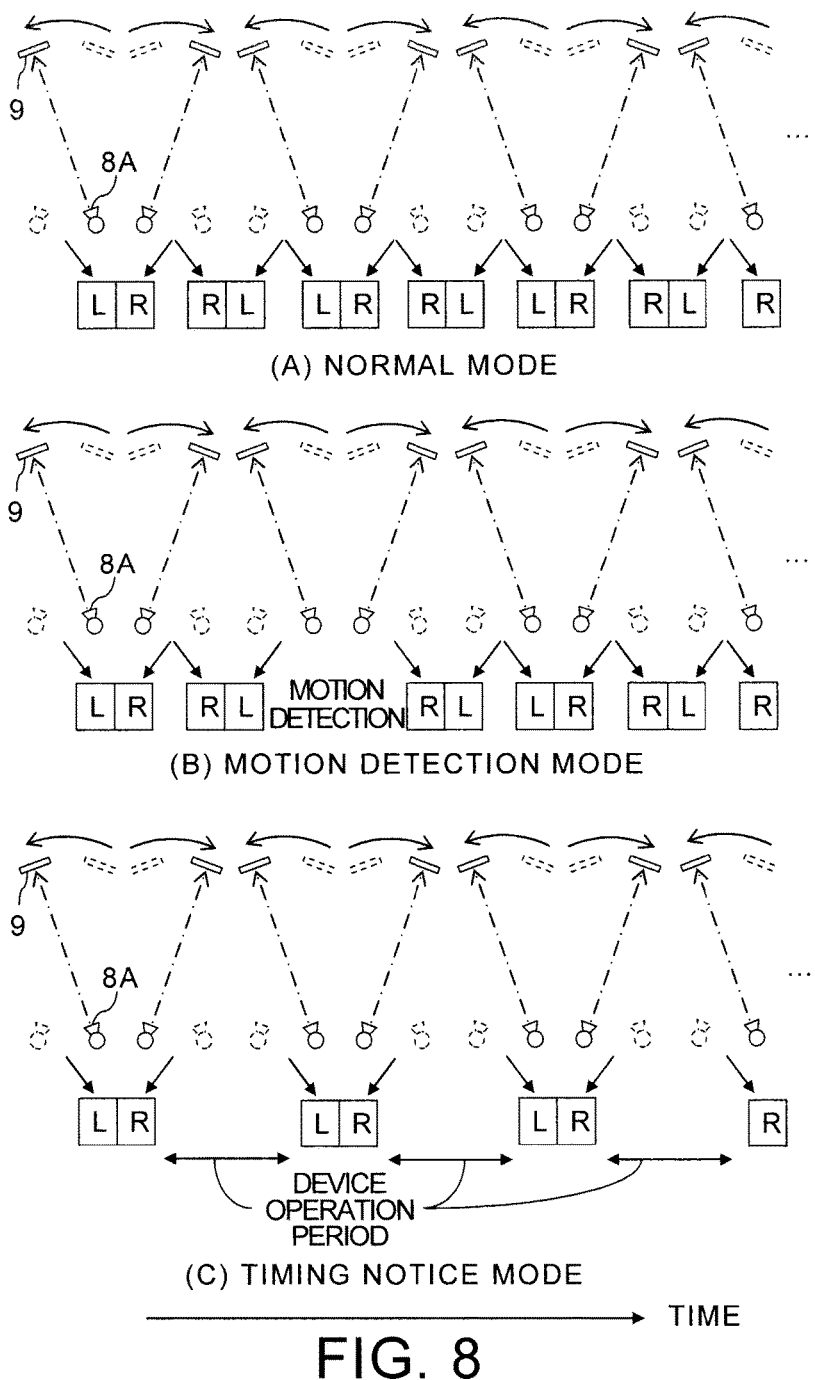
FIG. 8 shows methods of display processing for avoiding an influence of a motion in the display processing part shown in FIG. 1.

FIG. 8 shows methods of display processing for avoiding an influence of a motion in the display processing part 19 shown in FIG. 1.

In FIG. 8, the horizontal axis direction represents time. FIG. 8 (A) shows a display order of the images for left eye and the images for right eye in the case of acquiring X-ray images at the both end points of the imaging system 2 to display the stereoscopic images without display processing for avoiding influence of a motion. That is, when the X-ray tube 8A and the X-ray detector 9 are reciprocated to acquire X-ray image data at the both end points, the X-ray image data for left eye (L) and the X-ray image data for right eye (R) are acquired repeatedly and alternately.

Therefore, the X-ray image data for left eye (L) and the X-ray image data for right eye (R) can be displayed as a pair of two-parallax image data. Then, whenever X-ray image data is newly acquired, the X-ray image data for left eye (L) and the X-ray image data for right eye (R) can be updated. As this result, time series stereoscopic images that allow stereoscopic viewing from one direction can be displayed in real time.

However, when an imaging part has a motion between an acquisition timing of the X-ray image data for left eye (L) and an acquisition timing of the X-ray image data for right eye (R), images for which stereoscopic viewing is difficult may be displayed.

To solve this problem, as shown in FIG. 8 (B), when a motion of an imaging part has been detected by the motion detection part 19A, display processing to avoid displaying two frames of X-ray image data for left eye and for right eye acquired before and after a motion detection can be performed in the display processing part 19. The detection of a motion is feasible within about 100 ms of time. Therefore, immediately after detecting a motion, the display processing to avoid displaying the pair of two-parallax image data to be displayed next in order can be performed in real time.

In addition, it can be determined to avoid displaying X-ray image data corresponding to a period according to a timing of a motion detection. For example, not only X-ray image data acquired before and after a motion detection but several frames of X-ray image data corresponding to a period after a motion detection and so on may not be displayed.

Therefore, display processing may be performed so that a pair of two-parallax image data to be excepted from display targets is once generated, and subsequently the generated two-parallax image data is not displayed. Alternatively, display processing may be performed so that a pair of two-parallax image data to be excepted from display targets are not generated. That is, so long as at least X-ray image data necessary for a motion detection is generated, the X-ray image data to be excepted from display targets is not necessarily needed to be generated. Therefore, when the X-ray image data to be excepted from display targets is generated, the display processing part 19 has a function to extract frames of X-ray image data for stereoscopic viewing, acquired in a period without a motion, out of frames of X-ray image data, or a function to except X-ray image data for stereoscopic viewing, acquired in a period with a motion, out of frames of X-ray image data.

By such display processing in the display processing part 19, even when a user such as a doctor operates a device, only stereoscopic images in a period without a device motion can be selectively displayed. For this result, a user can continuously perform stereoscopic viewing of an imaging part with or without operations of a device.

On the other hand, the displaying period notice part 19B in the display processing part 19 has a function to output a notice of permission or prohibition of a motion in an imaging part of an object O, to an output unit, such as the display unit 7. Then, the display processing part 19 is configured to perform display processing not to generate or display stereoscopically visible image data corresponding to a period according to an output timing of the notice which permits or prohibits a motion in an imaging part.

FIG. 8 (C) shows an example of the display processing performed in the display processing part 19 with an output of notices which permit or forbid a motion in an imaging part. As shown in FIG. 8 (C), periods during which a device may be operated can be previously set as the device operation periods so that the displaying period notice part 19B can notify a user of at least one of the periods during which the device may be operated and the periods during which the device may not be operated.

A way of the notice is not only by displaying a message on the display unit 7 but also by outputting a sound message like "a wire may be moved now". Alternatively, a user may be notified of the period when a device may be moved or the period when a device may not be moved by changing a buzzer sound "beep-beep", which tells an X-ray exposure timing, into another sound.

Then, the display processing part 19 can perform display processing to generate stereoscopically visible image data, based on frames of X-ray image data acquired in periods according to an output timing of a notice by the displaying period notice part 19B, to display the generated image data on the display unit 7. For example, only two frames of X-ray image data acquired during a continuous period from just after an output timing of a notice prohibiting a motion in an imaging part to an output timing of a notice permitting a motion can be displayed for stereoscopic viewing as a pair of two-parallax image data. On the contrary, two frames of X-ray image data acquired during a continuous period from just after an output timing of a notice permitting a motion in an imaging part to an output timing of a notice prohibiting a motion can be excluded from displaying targets for stereoscopic viewing as a pair of two-parallax image data.

In the example shown in FIG. 8 (C), a notice to forbid a motion in an imaging part is output just before an acquisition of X-ray image data in the first direction. Next, X-ray image data in the second direction is acquired. Consequently, a pair of two-parallax image data is obtained. Furthermore, a notice to permit a motion in an imaging part is output just after the acquisition of the X-ray image data in the second direction. Then, a user, such as a doctor, can provide medical treatments by operating a device. Next, after a notice to forbid a motion in an imaging part is output once more, X-ray image data in the first direction is acquired. By such repetitions of a notice and an imaging, it becomes possible to display stereoscopic images without influence of a motion of an imaging part.

Figure 9:
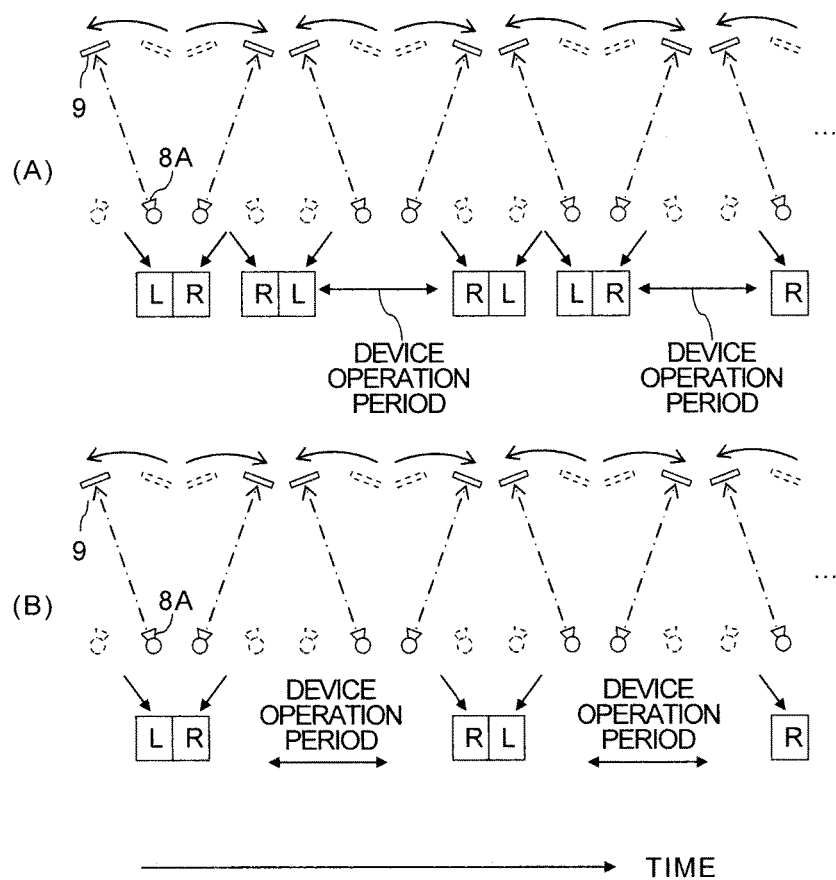
FIG. 9 shows modifications of the display control processing shown in FIG. 8 (C).

FIG. 9 shows modifications of the display control processing shown in FIG. 8 (C).

In FIG. 9, the horizontal axis direction represents time. The device operation period to allow a motion of an imaging part can be variably set as an arbitrary interval and length. For example, as shown in FIG. 9 (A), after a period when three frames of X-ray image data are continuously acquired, a device operation period may be set. Moreover, as shown in FIG. 9 (B), a period when a motion is permitted can also be lengthened by setting a device operation period including a period when an X-ray is exposed.

Note that, the examples where frames of X-ray image data are acquired at the both end points of the imaging system 2 have been described in FIG. 8 and FIG. 9. However, also in each case where X-ray image data is acquired during a movement of the imaging system 2 as shown in FIG. 2 (B), (C), (D), FIG. 4, FIG. 5, FIG. 6, and FIG. 7, a motion detection and/or setting a device operation period may be similarly performed between the acquisitions of the image data for left eye and the image data for right eye.

In addition to the method of the display processing for avoiding an influence of a motion as mentioned above, a control method of the imaging system 2 and a display method of stereoscopic images can be set up through the interface part 5 shown in FIG. 1. Especially, display processing for avoiding an influence of a motion may be switched between display processing modes. For that purpose, the interface part 5 has a function to display a setting screen of imaging conditions and display processing conditions for a stereoscopic display on the display unit 7, and also has a function to output setting information of various conditions, input by operating the input device 6 through the setting screen, to corresponding elements including the display processing part 19 and the control system 3.

For example, as shown in FIG. 8, the normal mode, the first processing mode and the second processing mode can be displayed as selectable modes on the setting screen of the display processing conditions. The normal mode is one in which display processing for avoiding an influence of a motion is not performed. The first processing mode is a motion detection mode in which stereoscopically visible image data corresponding to a period according to a timing of a motion detection are not generated or displayed in a case where a motion in an imaging part has been detected. The second processing mode is a timing notice mode in which a notice permitting or forbidding a motion in an imaging part is output to an output unit not to generate or display stereoscopically visible image data corresponding to a period according to an output timing of the notice. Then, a processing mode can be switched between plural processing modes including the first processing mode and the second processing mode according to information input from the input device 6.

While each display mode may be alternatively elective, the motion detection mode and the timing notice mode may be switchable between on and off. In this case, a motion detection and a timing notice of permission or prohibition of a motion are to be performed.

Therefore, when a motion in an imaging part has been detected by the motion detection part 19A during a period according to an output timing of a notice by the notice part 19B, display processing not to generate or display stereoscopically visible image data corresponding to a period according to a motion detection timing can be performed, for example. Alternatively, when at least one of the conditions, that a notice to forbid a motion in an imaging part has been output and that a motion in an imaging part has been detected, is met, the display processing not to generate or display stereoscopically visible image data can be performed.

Moreover, an interval between device operation periods and a length of a device operation period can be set through the interface part 5. That is, the interface part 5 functions as a specification part configured to specify display processing conditions to avoid an influence of a motion.

Next, an operation and an action of the X-ray imaging apparatus 1 will be explained.

First, the interface part 5 displays a setting screen of imaging conditions, including control methods of the imaging system 2, and display processing conditions of stereoscopically visible images, on the display unit 7. On this setting screen, various motions of the imaging system 2 as shown in FIG. 2 to FIG. 7 can be set and display modes shown in FIG. 8 and FIG. 9 can be selected. Therefore, a user can select appropriate operation conditions of the imaging system 2 and a suitable display mode of stereoscopic images by operating the input device 6 in consideration of conditions such as necessity of device operations, a required image quality, and exposure doses of the object O. Moreover, a user sets other imaging conditions required in order to acquire stereoscopic images of an imaging part of the object O or the like through the setting screen of imaging conditions.

On the other hand, an object O is set on the top plate of the bed 11. Moreover, a contrast agent is injected into the object O from the contrast medium injector 14, if needed. Then, the start of an imaging is directed to the interface part 5 with an operation of the input device 6. Thereby, the interface part 5 outputs the control information of the imaging system 2 to the control system 3 according to the set imaging conditions. On the other hand, the interface part 5 outputs information specifying the selected display mode to the display processing part 19.

Then, control signals corresponding to the imaging conditions are output from the imaging position control unit 13 of the control system 3 to drive the driving mechanism 7. Thereby, the X-ray exposure part 8 and the X-ray detector 9 move according to the imaging conditions.

On the other hand, a high voltage is applied to the X-ray tube 8A of the X-ray exposure part 8 from the high voltage generator 12 of the control system 3 according to the imaging conditions. Thereby, an X-ray is exposed to an imaging part of the object O from the X-ray tube 8A at timing at which the X-ray tube 8A and the X-ray detector 9 are on the predetermined position with the predetermined rotational angle. Then, the X-ray which transmitted the object O is detected by the X-ray detector 9.

Next, an X-ray detection signal is output to the medical image processing apparatus 16 from the X-ray detector 9 through the A/D converter 15. Thereby, the digitized X-ray detection data is acquired in the X-ray image generation part 17. Then, the X-ray image generation part 17 generates X-ray image data by known data processing of the X-ray detection data.

The X-ray image data generated in the X-ray image generation part 17 is given to the X-ray image acquisition part 18. Then, frames of X-ray image data corresponding to at least two X-ray exposure directions are acquired sequentially in the X-ray image acquisition part 18 in the same flow.

Next, the X-ray image acquisition part 18 gives the frames of the X-ray image data to the display processing part 19. Then, the display processing part 19 displays X-ray images, which can stereoscopically viewed, on the display unit 7 according to a display format of stereoscopic image. For example, in case of displaying an image for left eye and an image for right eye with a time division, X-ray image data acquired for left eye and X-ray image data acquired for right eye are subjected to the time division in the display processing part 19 to be output to the display unit 7.

Thereby, a user can stereoscopically view X-ray images displayed on the display unit 7 through the dedicated glasses 20. For example, when a pair of two-parallax images are repeatedly acquired at the same positions, stereoscopic images can be observed as a moving image. Alternatively, in the case where a pair of two-parallax images are repeatedly acquired and the acquisition positions of the pair of the two-parallax images change, stereoscopic images can be observed as a moving image whose observation direction changes with time.

In the case where the motion detection mode has been selected as the display mode, the motion detection part 19A determines existence of a motion between a pair of two-parallax image data based on the pair. Alternatively, in the case where a device with the sensor 21 has been inserted in the object O, the motion detection part 19A determines existence of a motion in an imaging part based on output signals from the sensor 21 received by the receiving antenna 22.

When a motion has been detected, a display of stereoscopic image using at least two-parallax image data acquired before and after a generating timing of the motion is not performed as shown in FIG. 8 (B) by display processing in the display processing part 19. After that, a display of stereoscopic image using two-parallax image data acquired at timings when a predetermined time has passed after the generating timing of the motion is performed.

Accordingly, a user can provide a medical treatment such as an endovascular treatment of the object O with operating a device freely. Moreover, even if the device is moved, stereoscopic images acquired in a period when the device is static are extracted to be selectively displayed on the display unit 7. Therefore, the user can perform a medical treatment with operating a device with referring to comfortable stereoscopic images.

On the other hand, in the case where the timing notice mode has been selected as the display mode, the displaying period notice part 19B outputs one or both of a notice to permit a motion and a notice to prohibit a motion at an interval previously set through the interface part 5. Thereby, the user can know a device operation period when a device may be moved.

Then, the display processing part 19 does not display stereoscopic images using two-parallax image data acquired in the device operation period as shown in FIG. 8 (C). In other words, the display processing part 19 displays two-parallax image data, acquired between a certain device operation period and the next device operation period, for stereoscopic viewing.

Accordingly, the user can provide a medical treatment for the object O with operating a device at a suitable timing by checking a notice to permit a motion or a notice to forbid a motion. Moreover, a stereoscopic image corresponding to a period without a device motion is intermittently indicated and updated on the display unit 7. Therefore, the user can perform a medical treatment with operating a device with referring to comfortable stereoscopic images.

That is, the above mentioned X-ray imaging apparatus 1 is configured to acquire frames of X-ray image data by reciprocating the single imaging system 2, and to display stereoscopic images by using frames of X-ray image data acquired in periods without a motion or a motion possibility in an imaging part of the object O.

Accordingly, even if an imaging part moved between acquisitions of two frames of X-ray image data for stereoscopic viewing, stereoscopic images can be generated and displayed with reducing an influence of the motion. Therefore, even in the example case where a doctor operates a device, such as a wire, for an endovascular treatment or the like, stereoscopic viewing of the device can be comfortably achieved.

Moreover, according to the X-ray imaging apparatus 1, stereoscopic images can be generated and displayed by using the single imaging system 2. In addition, the X-ray imaging apparatus 1 does not need complicate image reconstruction processing for generating and displaying stereoscopic images. Therefore, stereoscopic images can be generated and displayed by a very cheap and simple composition and data processing. In other words, even the X-ray imaging apparatus 1 having the single imaging system 2 can generate and display stereoscopic images which are not inferior to those which can be generated in an X-ray imaging apparatus having plural imaging systems or an X-ray imaging apparatus performing advanced image reconstruction processing.

Specifically, even when the X-ray imaging apparatus 1 cannot acquire image data for left eye and of image data for right eye at the same timing, stereoscopic images can be generated and displayed with reducing an influence of a motion of the object O similarly to an X-ray imaging apparatus that can simultaneously acquire image data for left eye and image data for right eye using plural imaging systems.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

For example, although a case where two-parallax images for a 3D image allowing stereoscopic viewing are acquired by using the X-ray imaging apparatus having the single imaging system has been explained in the above-mentioned example, similar two-parallax images can be also acquired in an X-ray imaging apparatus having plural imaging systems by using one of the plural imaging systems. That is, two-parallax images for a 3D image can be acquired by using an X-ray imaging apparatus which acquires X-ray image data of an object using at least one imaging system.

Furthermore, although the above-mentioned example explains the case where the control system 3 moves the imaging system 2 along with a locus of a pendulum on a plane, it is also possible to move the imaging system 2 so that a locus of the imaging system 2 becomes one of a pendulum when the locus of the imaging system 2 is projected on a plane. As a specific example, the imaging system 2 can be moved along with a locus having a shape of an ellipse or a character of eight. In this case, a high-speed imaging is attained since the imaging system 2 does not stand still.

What is claimed is:

1. An X-ray imaging apparatus comprising:
    an imaging system, including an X-ray tube and an X-ray detector, configured to generate X-ray image data of an object;
    a control system configured to control the imaging system to generate frames of X-ray image data corresponding to mutually different directions by reciprocating the imaging system repeatedly, the frames of the X-ray image data being generated in a first period including a period during which a motion of an imaging part of the object exists;
    a display processing circuit configured to acquire from said X-ray tube and said X-ray detector frames of X-ray image data for stereoscopic viewing out of the frames of the X-ray image data corresponding to the different directions to generate and display stereoscopically visible image data on a display unit based on the generated frames of the X-ray image data for the stereoscopic viewing, the frames of the X-ray image data for the stereoscopic viewing being generated in a second period without the motion or a possibility of the motion in the imaging part of the object, the second period being a part of the first period, the stereoscopically visible image data corresponding to frames of X-ray image data for left eye and right eye, wherein said display processing circuit is configured to detect motion in the imaging part of the object based on the frames of the X-ray image data generated by said imaging from said X-ray tube and said X-ray detector and to display the stereoscopically visible image data when no motion is detected; and
    wherein said display processing circuit is configured to output a notice to at least one of the display unit and another output device to avoid generating or displaying stereoscopically visible image data corresponding to a period according to an output timing of the notice, the notice being for permitting or prohibiting a possible motion in the imaging part.

2. An X-ray imaging apparatus comprising:
    an imaging system, including an X-ray tube and an X-ray detector, configured to generate X-ray image data of an object;
    a control system configured to control the imaging system to generate frames of X-ray image data corresponding to mutually different directions by reciprocating the imaging system repeatedly, the frames of the X-ray image data being generated in a first period including a period during which a motion of an imaging part of the object exists;
    a display processing circuit configured to acquire from said X-ray tube and said X-ray detector frames of X-ray image data for stereoscopic viewing out of the frames of the X-ray image data corresponding to the different directions to generate and display stereoscopically visible image data on a display unit based on the generated frames of the X-ray image data for the stereoscopic viewing, the frames of the X-ray image data for the stereoscopic viewing being generated in a second period without the motion or a possibility of the motion in the imaging part of the object, the second period being a part of the first period, the stereoscopically visible image data corresponding to frames of X-ray image data for left eye and right eye, wherein said display processing circuit is configured to detect motion in the imaging part of the object based on the frames of the X-ray image data generated by said imaging from said X-ray tube and said X-ray detector and to display the stereoscopically visible image data when no motion is detected; and
    wherein said display processing circuit is configured to output a notice to at least one of the display unit and another output device to avoid generating or displaying stereoscopically visible image data corresponding to a period according to a detection timing of the motion when the motion in the imaging part has been detected in a period according to an output timing of the notice, the notice being for permitting or prohibiting a possible motion in the imaging part.

3. An X-ray imaging apparatus comprising:
    an imaging system, including an X-ray tube and an X-ray detector, configured to generate X-ray image data of an object;
    a control system configured to control the imaging system to generate frames of X-ray image data corresponding to mutually different directions by reciprocating the imaging system repeatedly, the frames of the X-ray image data being generated in a first period including a period during which a motion of an imaging part of the object exists;
    a display processing circuit configured to acquire from said X-ray tube and said X-ray detector frames of X-ray image data for stereoscopic viewing out of the frames of the X-ray image data corresponding to the different directions to generate and display stereoscopically visible image data on a display unit based on the generated frames of the X-ray image data for the stereoscopic viewing, the frames of the X-ray image data for the stereoscopic viewing being generated in a second period without the motion or a possibility of the motion in the imaging part of the object, the second period being a part of the first period, the stereoscopically visible image data corresponding to frames of X-ray image data for left eye and right eye, wherein said display processing circuit is configured to detect motion in the imaging part of the object based on the frames of the X-ray image data generated by said imaging from said X-ray tube and said X-ray detector and to display the stereoscopically visible image data when no motion is detected;
    wherein said display processing circuit is configured to avoid generating or displaying stereoscopically visible image data corresponding to a period according to a detection timing of the motion when the motion of the imaging part has been detected; and wherein said display processing circuit is configured to detect the motion based on the frames of the X-ray image data generated by said imaging system.

4. An X-ray imaging apparatus of claim 3, wherein said display processing circuit is configured to avoid generating or displaying stereoscopically visible image data corresponding to a period according to a detection timing of the motion when the motion of the imaging part has been detected.

5. An X-ray imaging apparatus of claim 3, wherein said display processing circuit is configured to switch processing modes including a first processing mode and a second processing mode according to an information input from an input device, the first processing mode being to avoid generating or displaying stereoscopically visible image data corresponding to a period according to a detection timing of the motion when the motion in the imaging part has been detected, the second processing mode being to output a notice to at least one of the display unit and another output device to avoid generating or displaying stereoscopically visible image data corresponding to a period according to an output timing of the notice, the notice being for permitting or prohibiting a possible motion in the imaging part.

6. An X-ray imaging apparatus comprising:

an imaging system, including an X-ray tube and an X-ray detector, configured to generate X-ray image data of an object;

a control system configured to control the imaging system to generate frames of X-ray image data corresponding to mutually different directions by reciprocating the imaging system repeatedly, the frames of the X-ray image data being generated in a first period including a period during which a motion of an imaging part of the object exists;

a display processing circuit configured to acquire from said X-ray tube and said X-ray detector frames of X-ray image data for stereoscopic viewing out of the frames of the X-ray image data corresponding to the different directions to generate and display stereoscopically visible image data on a display unit based on the generated frames of the X-ray image data for the stereoscopic viewing, the frames of the X-ray image data for the stereoscopic viewing being generated in a second period without the motion or a possibility of the motion in the imaging part of the object, the second period being a part of the first period, the stereoscopically visible image data corresponding to frames of X-ray image data for left eye and right eye, wherein said display processing circuit is configured to detect motion in the imaging part of the object based on the frames of the X-ray image data generated by said imaging from said X-ray tube and said X-ray detector and to display the stereoscopically visible image data when no motion is detected, wherein said display processing circuit is configured to avoid generating or displaying stereoscopically visible image data corresponding to a period according to a detection timing of the motion when the motion of the imaging part has been detected; and wherein said display processing circuit is configured to detect the motion based on information from a sensor inserted in the imaging part.

7. An X-ray imaging apparatus of claim 6, wherein said control system is configured to move the imaging system along an ellipse or Figure eight locus, a projection of the locus on a plane becoming pendular.

8. An X-ray imaging apparatus comprising:

an imaging system, including an X-ray tube and an X-ray detector, configured to generate X-ray image data of an object;

a control system configured to control the imaging system to generate frames of X-ray image data corresponding to mutually different directions by reciprocating the imaging system repeatedly; and a display processing circuit configured to output a notice to at least one of a display unit and another output device to generate and display stereoscopically visible image data on the display unit based on frames of X-ray image data generated in a period according to an output timing of the notice, the notice being for permitting or prohibiting a possible motion in an imaging part of the object.

9. A medical image processing apparatus comprising:

an image acquisition circuit configured to generate frames of X-ray image data of an object corresponding to mutually different directions, the frames of the X-ray image data being generated by reciprocating a single imaging system repeatedly; and a display processing circuit configured to output a notice to at least one of a display unit and another output device to generate and display stereoscopically visible image data on the display unit based on frames of X-ray image data generated in a period according to an output timing of the notice, the notice being for permitting or prohibiting a possible motion in an imaging part of the object.

10. An X-ray imaging method comprising:

generating X-ray image data of an object by using an X-ray tube and an X-ray detector;

controlling the X-ray tube and the X-ray detector to generate frames of X-ray image data corresponding to mutually different directions by reciprocating the X-ray tube repeatedly;

detecting motion in the imaging part of the object based on the frames of the X-ray image data generated by the X-ray tube and the X-ray detector; and outputting a notice to at least one of a display unit and another output device to generate and display stereoscopically visible image data on the display unit based on frames of X-ray image data generated by the X-ray tube and the X-ray detector in a period according to an output timing of the notice, the notice being for permitting or prohibiting a possible motion in an imaging part of the object.

11. A medical image processing method comprising:

generating frames of X-ray image data of an object corresponding to mutually different directions, the frames of the X-ray image data being generated by reciprocating a single imaging system repeatedly; and outputting a notice to at least one of a display unit and another output device to generate and display stereoscopically visible image data on the display unit based on frames of X-ray image data generated in a period according to an output timing of the notice, the notice being for permitting or prohibiting a possible motion in an imaging part of the object.

* * * * *